(12) United States Patent
Stern et al.

(10) Patent No.: US 7,214,532 B2
(45) Date of Patent: May 8, 2007

(54) METHODS FOR IDENTIFYING HUMAN CELL LINES USEFUL FOR ENDOGENOUS GENE ACTIVATION, ISOLATED HUMAN CELL LINES IDENTIFIED THEREBY, AND USES THEREOF

(75) Inventors: Anne Stern, Penzberg (DE); Michael Brandt, Iffeldorf (DE); Konrad Honold, Penzberg (DE); Johannes Auer, Penzberg (DE); Hans Koll, Weilheim (DE); Reinhard Franze, Penzberg (DE); Ulrich Pessara, Weilheim (DE)

(73) Assignee: Roche Diagnostics, GmbH, Mannheim (DE)

( * ) Notice: Subject to any disclaimer, the term of this patent is extended or adjusted under 35 U.S.C. 154(b) by 478 days.

(21) Appl. No.: 10/351,397

(22) Filed: Jan. 27, 2003

(65) Prior Publication Data
US 2004/0203001 A1 Oct. 14, 2004

Related U.S. Application Data

(63) Continuation of application No. 09/113,692, filed on Jul. 10, 1998, now Pat. No. 6,548,296.

(30) Foreign Application Priority Data

| Jul. 23, 1997 | (EP) | ................................... 97112640 |
| Dec. 1, 1997 | (EP) | ................................... 97121073 |
| Dec. 3, 1997 | (EP) | ................................... 19753681 |

(51) Int. Cl.
*C12N 15/00* (2006.01)
(52) U.S. Cl. .................................... 435/320.1; 435/463
(58) Field of Classification Search .................... None
See application file for complete search history.

(56) References Cited

U.S. PATENT DOCUMENTS

| 4,806,524 A | 2/1989 | Kawaguchi et al. |
| 4,992,419 A | 2/1991 | Woog et al. |
| 6,391,633 B1 * | 5/2002 | Stern et al. .................. 435/335 |
| 6,565,844 B1 * | 5/2003 | Treco et al. ................ 435/69.1 |
| 2003/0148465 A1 * | 8/2003 | Chan et al. ................. 435/69.1 |

FOREIGN PATENT DOCUMENTS

WO    WO 96/19573    6/1996

* cited by examiner

*Primary Examiner*—James Ketter
(74) *Attorney, Agent, or Firm*—Fulbright & Jaworski LLP

(57) ABSTRACT

The invention concerns human cells which, due to an activation of the endogenous human EPO gene, are able to produce EPO in an adequate quantity and purity to enable a cost-effective production of human EPO as a pharmaceutical preparation. Furthermore the invention concerns a process for the production of such human EPO-producing cells, DNA constructs for the activation of the endogenous EPO gene in human cells as well as a process for the large-scale production of EPO in human cells.

5 Claims, 9 Drawing Sheets

Gene Activation Sequence

SEQUENCE LISTING

```
<160> NUMBER OF SEQ ID NOS: 10

<210> SEQ ID NO 1
<211> LENGTH: 32
<212> TYPE: DNA
<213> ORGANISM: Homo sapiens

<400> SEQUENCE: 1
cgcggcggat cccagggagc tgggttgacc gg                                 32

<210> SEQ ID NO 2
<211> LENGTH: 38
<212> TYPE: DNA
<213> ORGANISM: Homo Sapiens

<400> SEQUENCE: 2
ggccgcgaat tctccgcgcc tggccggggt ccctcagc                           38

<210> SEQ ID NO 3
<211> LENGTH: 36
<212> TYPE: DNA
<213> ORGANISM: Homo Sapiens

<400> SEQUENCE: 3
cgccgcggat cctctcctcc ctcccaagct gcaatc                             36

<210> SEQ ID NO 4
<211> LENGTH: 36
<212> TYPE: DNA
<213> ORGANISM: Homo Sapiens

<400> SEQUENCE: 4
ggccgcgaat tctagaacag atagccaggc tgagag                             36

<210> SEQ ID NO 5
<211> LENGTH: 4
<212> TYPE: PRT
<213> ORGANISM: Homo Sapiens
<220> FEATURE:
<221> NAME/KEY: Variant
<223> OTHER INFORMATION: The first Xaa is Gly or Ser.  The second Xaa is
```

```
              Ala,
<223> OTHER INFORMATION: Val, Leu, Ile, Ser, or Pro.  The third Xaa is
      Pro,
<223> OTHER INFORMATION: Arg, Cys or His

<400> SEQUENCE: 5

Met Xaa Xaa Xaa
  1

<210> SEQ ID NO 6
<211> LENGTH: 4
<212> TYPE: PRT
<213> ORGANISM: Homo Sapiens

<400> SEQUENCE: 6

Met Gly Val His
  1

<210> SEQ ID NO 7
<211> LENGTH: 4
<212> TYPE: PRT
<213> ORGANISM: Homo Sapiens

<400> SEQUENCE: 7

Met Gly Ala His
  1

<210> SEQ ID NO 8
<211> LENGTH: 4
<212> TYPE: PRT
<213> ORGANISM: Homo Sapiens

<400> SEQUENCE: 8

Met Ser Ala His
  1

<210> SEQ ID NO 9
<211> LENGTH: 4
<212> TYPE: PRT
<213> ORGANISM: Homo Sapiens

<400> SEQUENCE: 9

Met Gly Val Pro
  1

<210> SEQ ID NO 10
<211> LENGTH: 4
<212> TYPE: PRT
<213> ORGANISM: Homo Sapiens

<400> SEQUENCE: 10

Met Ser Val His
  1
```

METHODS FOR IDENTIFYING HUMAN CELL LINES USEFUL FOR ENDOGENOUS GENE ACTIVATION, ISOLATED HUMAN CELL LINES IDENTIFIED THEREBY, AND USES THEREOF

This application is a continuation of application Ser. No. 09/113,692 filed Jul. 10, 1998 now U.S. Pat. No. 6,548,296.

FIELD OF THE INVENTION

The invention relates to methods for identifying human cells useful in endogenous gene activation, in order to produce human proteins. The invention also involves processes for manufacture of proteins, such as human proteins in cells identified in this manner, as well as the isolated cells so identified.

BACKGROUND AND PRIOR ART

The production of human proteins by endogenous gene activation in a human cell line is known. See, e.g., WO 93/09222, WO 94/12650 and WO 95/31560 for example, describing the production of human erythropoietin and other human proteins in human cell lines by endogenous gene activation.

These references do not advise, however, as to what criteria have to be observed when selecting cells used to produce human proteins. In fact, the methods described in these references do not ensure high yield and contaminant free production of human protein. In fact, only low yields of human proteins are achieved following the above cited references.

As noted, supra, human erythropoietin is described in these references as a protein, the production of which is desired. A discussion of erythropoietin and the art relating to its production is set forth here, although it is to be borne in mind that erythropoietin production is simply exemplary of the invention, which is in no way limited to this protein.

Erythropoietin ("EPO" hereafter) is a glycoprotein which stimulates the production of red blood cells. EPO is present only in very low concentrations in the blood plasma of healthy persons, so it is not possible to prepare large amounts via purification of plasma. EP-B-0148 605 and EP-B-0205 564, incorporated by reference, describe the production of recombinant human EPO in Chinese Hamster ovary, or "CHO" cells. The EPO described in EP-B-0148 605 has a higher molecular weight than EPO purified from urine and is not O-glycosylated. The EPO from CHO cells described in EP-B-0 205 564 is available in large amounts and in pure form, but it is derived from non-human cells. Further, the production yield of CHO cells is also often relatively limited.

As alluded to supra, it is known that human EPO ("hEPO") can be isolated from the urine of patients with aplastic anemia (Miyake et al., *J. Biol. Chem.* 252 (1977), 5558–5564). A seven-step process is disclosed in this reference, which involves, inter alia, ion exchange chromatography, ethanol precipitation, gel filtration and adsorption chromatography. In this process an EPO preparation with a specific activity of ca. 70,000 U/mg protein is obtained in a 21% yield. The disadvantages of this process and other processes for isolating urinary EPO include obtaining the starting material in adequate amounts and with a reproducible quality. Furthermore, the purification of hEPO from urine is difficult and even a purified product is not free of urinary impurities.

GB-A-2085 887, incorporated by reference, describes a process for the production of human lymphoblastoid cells which are able to produce EPO in small amounts. It is not possible to economically produce EPO of the desired quality using the human lymphoblastoid cells disclosed herein.

WO 91/06667 as noted supra, describes a process for the recombinant production of EPO. In this process the endogenous EPO gene is operatively linked to a viral promoter in a first process step by homologous recombination, in primary human embryonic kidney cells. The recombined DNA is then isolated from these cells. In a second step, the isolated DNA is transformed into CHO cells, and the expression of EPO in these cells is analyzed. There is no indication that it is possible to produce EPO in human cells.

WO 93/09222 describes the production of EPO in human cells. In this process relatively high levels of EPO production, i.e., up to 960,620 mU/$10^6$ cells/24 hours is achieved using human fibroblasts which have been transfected with a vector containing the complete EPO gene. These transfected cells contain an exogenous EPO gene which is not located at the correct EPO gene locus, leading to problems with respect to the stability of the cell line. The reference does not discuss constitutive EPO production. Moreover, there is also no information about whether the EPO produced is of sufficient quality for, e.g., pharmaceutical use.

Activation of the endogenous EPO gene in human HT1080 cells is also described in this reference, but production of only 2,500 mU/$10^6$ cells/24 hours (corresponding to ca. 16 ng/$10^6$ cells/24 hours) is found. Such low production levels are unsuitable for economic production of a pharmaceutical preparation.

WO 94/12650 and WO 95/31560, incorporated by reference, describe that a human cell with an endogenous EPO gene activated by a viral promoter is capable, after amplification of the endogenous EPO gene, of producing EPO in an amount of up to ca. 100,000 mU/$10^6$ cells/24 hours (corresponding to ca. 0.6 µg/$10^6$ cells/24 hours). Even this amount is still not sufficient for the economic production of a pharmaceutical preparation.

As indicated, supra, the cells and cell lines disclosed in the literature relating to endogenous gene activation, while useful, are by no means totally satisfactory. It has now been found, however, that it is possible to identify and to isolate cells and cell lines which will be useful in high yield production of proteins, following endogenous gene activation via, e.g., homologous recombination. Hence, one aspect of the invention is a method for identifying such cells and cell lines. A second feature of the invention are the cells and cell lines so identified. Yet a third feature of the invention is the use of the cells and cell lines for the production of proteins, using these cells and cell lines. How these and other aspects of the invention are achieved will be seen from the disclosure which follows.

DETAILED DESCRIPTION OF PREFERRED EMBODIMENTS

Figure 1:
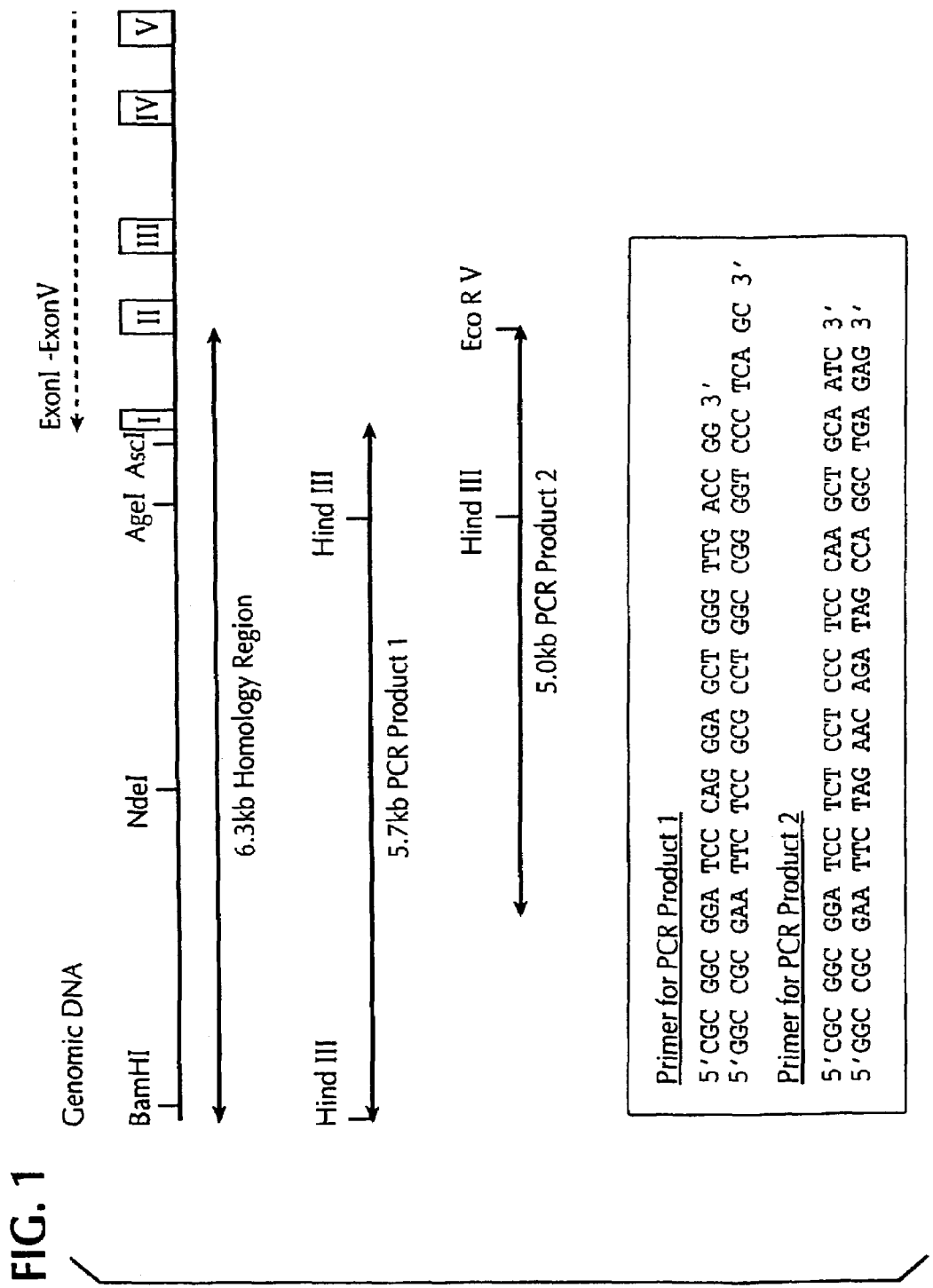
FIG. 1 shows a schematic representation of the amplification of homology regions of the EPO gene from the region of the 5' untranslated sequences, exon 1 and intron 1, and primers SEQ ID NOS:1–4.

As indicated, supra, one feature of this invention is a method for identifying and isolating cells and cell lines, preferably human cells and cell lines, which are useful in the production of endogenous proteins via gene activation, preferably by homologous recombination. In the method, a cell or cell line, preferably human, is first tested to determine if the desired gene of interest, which will generally correspond to the naturally occurring nucleotide sequence, is present. The details of how this is determine and are set forth, infra. If it is determined that the cell or cell line contains the desired sequence, then it is determined if a population of the cell or cell line doubles, at least five times, in a period of 14 days, when incubated in suspension culture. If the cell or cell line satisfies this criterion, then it is tested to see if a population of the cell or cell line will double, at least five times over 14 days if grown in serum free culture medium. If the cell or cell line satisfies this criterion, then it will be useful in activation of the gene of interence, via, e.g., homologous recombination.

It is preferred that the starting materials are immortalized human cell lines. These are preferred because they have known advantages with respect to culturability which need not be summarized here. Such cell lines, it must be borne in mind, can exhibit mutations in their genomes, so the presence of the desired sequence must be confirmed. The polymerase chain reaction, or "PCR," for example, can be used to determine this, following standard protocols.

Assuming the cell or cell line possesses the desired sequence, it is tested for its ability to be cultured. Suspended cells are easier to ferment and the fermentation can be more easily adapted to larger dimensions, such as large fermenters with a volume of 10 to 50,000 liters. Consequently, the selected cells should either be cells which are known to be culturable in suspension or they should be readily adaptable to suspension culture. One determines this by culturing the cells for 14 days while stirring continuously. If the population of the cells doubles at least five times within this period, they are regarded as being suitable for the next step of the invention. The number of population doublings can be determined by periodic determinations of the cell count, e.g., by mechanical cell counting or by measuring the optical density of the cell suspension.

A further important feature of the cells or cell lines of the invention is the culturability in serum-free medium. Since the purification of proteins from serum-free cell cultures is considerably simpler, and in serum-free culture there is no risk of contamination with animal pathogens such as viruses, it should be possible to culture the selected cells in serum-free culture. To determine this, the cells are cultured for 14 days at a density of 1 to $10 \times 10^5$ cells per ml in culture vessels containing serum-free medium (e.g., RPMI 1640 containing insulin, transferrin and selenide). If the population of the cells doubles at least five times during this culture period, determined as above, they are regarded as being suitable for serum-free culture.

A further important feature of the invention, representing a preferred embodiment, is the generation time. The selected cells should exhibit a high proliferation in media such as DMEM, 10% fetal calf serum or RPMI 1640 containing 10% fetal calf serum, i.e., within one week in culture their population should double 10 to 256 times, preferably 64 to 128 times. To determine this, the cells are seeded in culture plates at a concentration of 0.1 to $10 \times 10^5$ cells per ml, preferably 0.5 to $2 \times 10^5$ cells per ml and the cell count is determined every two to three days with the aid of a cell counting chamber after or without trypsinization. Cells which have a sufficiently short generation time are particularly suitable for large-scale production of human proteins by endogenous gene activation.

A further preferred embodiment of the invention is the absence of detectable endogenous expression, i.e., transcription and translation, of the target gene. Preferably, those cell lines are selected for endogenous gene activation which have essentially no or no endogenous expression of the target gene. To determine this, the cells are seeded at a cell density of 0.01 to $2 \times 10^6$ cells/ml, preferably 0.5 to $1 \times 10^6$ cells/ml of culture medium. After a predetermined time period, e.g., 24 hours, the cell supernatant is removed, the cells are discarded and the content of the target protein is determined in the cell supernatant by means of known test procedures, e.g., ELISA. In the case of EPO, the detection limit may be 10 pg/EPO/ml. Cells which yield less than 10 pg protein when seeded at $10^5$ cell/ml are regarded as non-producers and are particularly suitable.

It is especially preferred that the target gene exhibit polysomy in the selected cell. The presence of more than two chromosomal copies of the target gene in the cell significantly increases the yield of protein, following homologous recombination. The cells Namalwa (Nadkarni et al, Cancer 23 (1969), 64–79) or HeLa S3 (Puck et al., J. Exp. Med. 103 (1956), 273–284) which possess three copies of chromosome 7 have proven to be particularly suitable for the production of EPO, whose gene lies on chromosome 7.

Further examples of cell lines that contain more than one copy of chromosome 7 are the colon adenocarcinoma cell line SW-480 (ATCC CCL-288; Leibovitz et al., *Cancer Res.* 36 (1976), 4562–4567), the malignant melanoma cell line SK-MEL-3 (ATCC HTB 69; Fogh and Tremp, in: Human Tumor Cells in vitro, pp 115–159, *J. Fogh (ed.)*, Plenum Press, New York 1975), the colon adenocarcinoma cell Colo-320 (ATCC CCL-220; Quinn et al., *Cancer* Res. 39 (1979), 4914–4924)), the melanoma cell line MEL-HO (DSM ACC 62; Holzmann et al., *Int. J. Cancer* 41 (1988), 542–547) and the kidney carcinoma cell line A-498 (DSM ACC 55; Giard et al., *J. Natl. Cancer Inst.* 51 (1973), 1417–1423).

The number of chromosomes in the genome of a cell line can be determined by using DNA probes which are specific for the respective chromosome or/and the locus of the target gene.

It is especially preferred that the cell line used for endogenous gene activation correctly glycosylates the desired target protein. A human cell line which synthesizes the target protein with a glycosylation pattern which is comparable to and is preferably indistinguishable from the naturally occurring target protein, especially in the number of sialic acid residues is particularly preferred. The ability to correctly glycosylate can be tested by transiently transfecting the cell of interest with, e.g., a vector such as an extrachromosomal vector which contains the desired target gene under the control of a promoter that is active in the cell. After transient expression of the target gene the cell supernatant or/and the cell lysate is analyzed by isoelectric focusing. The presence of correct glycosylation can be easily determined. For example, non-glycosylated EPO, i.e., recombinant EPO from *E. coli* cells, has activity comparable to glycosylated EPO in vitro experiments. However, in vivo experiments, non-glycosylated EPO is considerably less effective. In order to determine whether a starting cell line is able to produce EPO with correct glycosylation, comparison can be made to urinary EPO, or with recombinant EPO from CHO cells, which is known to have a form of glycosylation which is active in humans and whose glycosylation is substantially identical to that of urinary EPO. Glycosylation is preferably compared by isoelectric focusing.

It is preferred that the cell line be free of infectious contamination, i.e., infectious viral particles or mycoplasmas. The examination for the presence of viral contamination can be carried out by means of cell culture, in vivo analyses or/and detection of specific viral proteins.

Cells or cell lines so identified can be used in a process for the production of human proteins by endogenous gene activation of a human cell line, which meets the above listed criteria.

The process according to the invention can be used to produce substances such as EPO, thrombopoietin (TPO), colony-stimulating factors such as G-CSF or GM-CSF, proteins which influence blood coagulation such as t-PA, interferons such as IFN-α, IFN-β or IFN-γ, interleukins such as IL-1 to IL-18, chemokines such as MIP, neurotrophic factors such as NGF or BDNF, proteins which influence bone growth such as IFG-BPs, hedgehog proteins, tumor growth factors such as TFG-β, growth hormones such as hGH, ACTH, enkephalins, endorphins, receptors such as interleukin or insulin receptors in soluble or/and membrane-bound forms and other protein binding proteins. The process is particularly preferably used to produce EPO.

Endogenous gene activation can be carried out according to known methods. Preferably, it comprises the steps:

(a) providing human starting cell lines which contain at least one copy of an endogenous target gene with the desired nucleic acid sequence and which have been identified as being suitable for the expression of the target gene via the processes described supra.

(b) transfecting the cells with a DNA construct comprising:
  (i) two flanking DNA sequences which are homologous to regions of the target gene locus in order to allow homologous recombination,
  (ii) a positive selection marker gene,
  (iii) optionally a negative selection marker gene,
  (iiii) optionally an amplification gene and
  (v) a heterologous expression control sequence which is active in the human cell, (c) culturing the transfected cells under conditions in which a selection takes place for the presence of the positive selection marker gene and optionally for the absence of the negative selection marker gene, (d) analyzing the cells that can be selected according to step (c), (e) identifying the cells producing the desired target protein and (f) optionally amplifying of the target gene in the selected cells.

The DNA construct used to produce the cell producing the desired human protein contains two flanking DNA sequences homologous to regions of the target gene locus. Suitable flanking sequences can be selected for in accordance with the methods described in WO 90/11354 and WO 91/09955. The flanking sequences preferably are at least 150 bp long. The homologous DNA sequences are particularly preferably selected from the 5' region of the target gene, e.g., 5'-untranslated sequences, signal-sequence-coding exons and introns located in this region, e.g., exon 1 and intron 1.

The positive selection marker gene can be any selection marker gene suitable for eukaryotic cells which leads to a selectable phenotype when expressed. Antibiotic resistance, auxotrophy etc. are examples of this. A particularly preferred positive selection marker gene is the neomycin phosphotransferase gene.

A negative selection marker gene can be present, but is not required. Examples of these include HSV thymidine kinase gene, expression of which leads to death in the presence of a selection agent. The negative selection marker gene is located outside of the two flanking homologous sequence regions, and is preferably downstream of the 3' homology region.

If amplification of the endogenously activated target gene in the human cell is desired, the DNA construct is provided with an amplification gene. Examples of suitable amplification genes are the dihydrofolate reductase gene, the adenosine deaminase gene, the ornithine decarboxylase gene, etc. A particularly preferred amplification gene is the dihydrofolate reductase gene, more particularly a gene coding for a dihydrofolate reductase arginine mutant which has higher sensitivity for the selective agent (methotrexate) than the wild-type gene. See Simonsen et al., *Proc. Natl. Acad. Sci. USA* 80 (1983), 2495, incorporated by reference.

It is especially preferred that the DNA construct used for the endogenous gene activation contains a heterologous expression control sequence that is active in a human cell. The expression control sequence comprises at least a promoter and preferably further sequences which improve expression, such as enhancer sequences. The promoter can be a regulatable or constitutive promoter. The promoter is preferably a strong viral promoter, e.g., an SV40 or a CMV promoter. The CMV promoter/enhancer is particularly preferred.

Endogenous genes as used herein refers to an endogenous gene not modified in the region which encodes the desired, mature polypeptide.

In accordance with the invention, one can isolate a human cell which contains a copy of an endogenous EPO gene in operative linkage with a heterologous expression control sequence that is active in the human cell and which is capable of producing at least 200 ng EPO/$10^6$ cells/24 hours without prior gene amplification. Such human cells preferably produce 200 to 3000 ng EPO/$10^6$ cells/24 hours and are most preferably able to produce 1000 to 3000 ng EPO/$10^6$ cells/24 hours, under appropriate culture conditions.

Human cells which contain several copies of an endogenous EPO gene, each in operative linkage with a heterologous expression control sequence that is active in the human cell and are able to produce at least 1000 ng EPO/$10^6$ cells/24 hours, are also a facet of the invention. Such human cell lines preferably produce 1,000 to 25,000 ng EPO/$10^6$ cells/24 hours and most produce 5,000 to 25,000 ng EPO/$10^6$ cells/24 hours under appropriate culture conditions.

The human cells and cell lines of the invention can be of any cell type, provided that they are culturable in vitro, in serum free medium, particularly in suspension culture. In this manner, it is possible to produce EPO in large fermenters of about 1,000 liters or more.

Preferably, immortalized cells such as HT 1080 cells (Rasheed et al., *Cancer* 33 (1974), 1027–1033), HeLa S3 cells (Puck et al., *J. Exp. Med.* 103 (1956), 273–284), Namalwa cells (Nadkarni et al., *Cancer* 23 (1969), 64–79) or a cell derived therefrom are used. HT1080 cells, HeLa S3 cells, and cells derived therefrom are especially preferred.

The cells of the invention are characterized by linkage of the endogenous EPO gene to a heterologous expression control sequence that is active in the human cell. The expression control sequence comprises a promoter, and preferably, further sequences that improve expression, such as enhancer sequences. The promoter can be a promoter that can be regulated, or a constitutive promoter. The promoter is preferably a strong viral promoter, e.g., an SV40 promoter, or a CMV promoter. The CMV promoter/enhancer is particularly preferred.

Furthermore, in order to optimize expression of proteins such as EPO, it is preferable that the endogenous gene in the human cell that is in operative linkage with the heterologous promoter have a signal peptide coding sequence which is different from the natural signal-peptide-coding sequence, and preferably codes for a signal peptide with a modified amino acid sequence. A signal-peptide-coding sequence which codes for a signal peptide sequence that is modified in the region of the four first amino acids. These first four amino acids satisfy the formula:

Met Xaa Xaa Xaa (SEQ ID NO:5)

wherein the first Xaa is Gly or Ser, the second Xaa is Ala, Val, Leu, Ile, Ser or Pro, and the third Xaa is Pro, Arg, Cys, or His, with the proviso that this four amino acid sequence is not Met Gly Val His (SEQ ID NO:6).

Particularly preferred are:

(a)　　Met-Gly-Ala-His　　(SEQ ID NO:7),

-continued (b)　　Met-Ser-Ala-His　　(SEQ ID NO:8), (c)　　Met-Gly-Val-Pro　　(SEQ ID NO:9) or (d)　　Met-Ser-Val-His　　(SEQ ID NO:10)

The sequence of the first four amino acids of the signal peptide is especially preferably Met-Ser-Ala-His (SEQ ID NO:8).

A further aspect of the present invention is a DNA construct useful for activating an endogenous EPO gene in a human cell comprising:

(i) two flanking DNA sequences which are homologous to regions of the human EPO gene locus, selected from 5' untranslated sequences, exon 1 and intron 1, in order to allow homologous recombination wherein a modified sequence is present in the region of exon 1 which codes for a four amino acid sequence as described supra;

(ii) a positive selection marker gene, (iii) a heterologous expression control sequence which is active in a human cell and (iv) optionally an amplification gene.

A further aspect of the present invention is a DNA construct for activating an endogenous EPO gene in a human cell comprising:

(i) two flanking DNA sequences which are homologous to regions of the human EPO gene locus and are selected from 5' untranslated sequences, exon 1 and intron 1 in order to allow a homologous recombination, (ii) a positive selection marker gene, (iii) a heterologous expression control sequence which is active in a human cell wherein the distance between the heterologous expression control sequence and the translation start of the EPO gene is not more than 1100 bp and (iv) optionally an amplification gene.

Surprisingly it has been found that when the EPO signal sequence is modified and/or when the distance between the heterologous expression control sequence and the translation start of the EPO gene is shortened, optimized expression is obtained. The distance between the promoter of the heterologous expression control sequence and the translation start of the EPO gene is preferably not more than 1100 bp, particularly preferably not more than 150 bp and most preferably not more than 100 bp. A particularly preferred example of a DNA construct that can be used according to the invention is the plasmid p189 (DSM 11661, DSMZ-Deutsche Sammlung Von Mikroorganismen Und Zelikulturen GmbH, Mascheroder Weg 1b, D-38124 Braunschweig, GERMANY, deposited 16 Jul. 1997) or a plasmid derived therefrom.

Yet a further aspect of the present invention is a process for the production of human EPO in which a human cell according to the invention is cultured in a suitable medium under conditions in which production of EPO takes place and the EPO is isolated from the culture medium. A serum-free medium is preferably used as the medium. The cells are preferably cultured in suspension. The production preferably takes place in a fermenter in particular in a large fermenter with a volume of for example 10–50,000 liters.

The isolation of human EPO from the culture medium of human cell lines preferably comprises the following steps:

(a) passing the cell culture supernatant over an affinity chromatography medium and isolating the fractions containing EPO, (b) optionally passing the fractions containing EPO over a hydrophobic interaction chromatography medium and isolating the fractions containing EPO, (c) passing the fractions containing EPO over hydroxyapatite and isolating the fractions containing the EPO and (d) concentrating and/or passing over a reverse phase (RP)-HPLC medium.

Step (a) of the purification process comprises passing the cell culture supernatant, which can optionally be pretreated, over an affinity chromatography medium.

Preferred affinity chromatography media are those on which a blue dye is coupled. A particularly preferred example is blue-Sepharose. After elution from the affinity chromatography medium the eluate containing EPO is optionally passed over a hydrophobic interaction chromatography medium. This step is expedient if a culture medium with a serum content >2% (v/v) is used. If a culture medium is used with a low serum content, e.g., 1% (v/v) or a serum-free medium, this step can be omitted. A preferred hydrophobic interaction chromatography medium is butyl-Sepharose.

The eluate from step (a) or—if used—step (b) is passed over hydroxyapatite in step (c) of the process according to the invention and the eluate containing EPO is subjected to a concentration step or/and a reverse phase HPLC purification step. The concentration is preferably carried out by exclusion chromatography, such as membrane filtration and the use of a medium, such as a membrane with an exclusion size of 10 kD has proven to be favorable.

An isolated human EPO with a specific activity of at least 100,000 U/mg protein in vivo (normocytaemic mouse) is obtainable by the process according to the invention which is free of urinary impurities and may or may not differ in its glycosylation from recombinant EPO from CHO cells. Preferably, the EPO of the invention has specific activity of at least 175,000, more preferably at least 200,000, and up to about 400–450,000 IU/mg of protein. The human EPO which is obtainable by the process according to the invention can contain α-2,3-linked or/and α-2,6-linked sialic acid residues. When EPO obtained from cells which contain an endogenously activated EPO gene was examined, the presence of α-2,3-linked and α-2,6-linked sialic acid residues was found. Furthermore, it was found that human EPO according to the invention has a content of less than 0.2% N-glycol-neuraminic acid relative to the content of N-acetyl neuraminic acid.

The purity of the human EPO obtained in accordance with the invention is at least 90%, more preferably at least 95% and most preferably at least 98% relative to the total protein content. The total protein content can be determined by reverse phase HPLC, e.g., with a Poros R/2H column.

Human species of proteins, such as EPO can be obtained by the process according to the invention which differ in their amino acid sequence. Thus for example using mass spectrometric analysis (MALDI-MS) it was found that a human EPO can be isolated from HeLa S3 cells wherein the isolated EPO consists essentially of a polypeptide with a length of 165 amino acids which is formed by C-terminal processing of an arginine residue. Up to about 15% of the recovered EPO may be 166 amino acids in length, depending on the culture conditions used. In addition a human EPO can also be obtained which consists of a polypeptide with a length of 166 amino acids, i.e., a non-processed EPO. Human EPO from Namalwa cells was isolated which contained a mixture of polypeptides with a length of 165 and 166 amino acids.

Such proteins, such as human EPO, can be used as an active substance for a pharmaceutical preparation which can optionally contain further active substances as well as standard pharmaceutical auxiliary, carrier and additive substances.

A further aspect of the present invention is an isolated nucleic acid molecule which codes for a human EPO with a modified sequence in the region of the first 4 amino acids of the signal peptide as described supra.

Genomic DNA and cDNA are both a part of the invention.

How these and other features of the invention are achieved will be seen in the examples which follow.

EXAMPLE 1

1. Culture

Cell lines were seeded at a concentration of $0.1–5 \times 10^5$ per ml, preferably $0.5–2 \times 105$ cells per ml in culture plates containing DMEM and 10% FCS or RPMI 1640 and 10% FCS and the cell count was determined every two to three days during culture with a counting chamber, with or without trypsinization, in a medium recommended for the respective cells and under suitable conditions. Cells which exhibited 16 to 256 population doublings, preferably 64 to 128 population doublings, within one week culture were assessed as positive (+, ++ or +++).

1.2 Ability to Culture in Suspension

In order to determine the ability to culture the cells in suspension, samples were cultured for 14 days at 37° C. and 7% $CO_2$ while stirring continuously in medium as above with and without the addition of serum, e.g., fetal calf serum. Cells which exhibited at least 5 population doublings during this phase were assessed as being suitable (+) for a suspension culture.

1.3 Ability to Culture in Serum-free Medium

In order to determine whether the cells could be cultured in serum free medium, they were cultured under conditions according to 1.1 for 14 days at a density of $1–10 \times 10^5$ cells/ml in culture vessels in the basic medium (without serum supplementation). Cells whose population doubled at least 5 times during this period (determined by cell counting) were assessed as being suitable (+) for serum-free culture.

1.4 Determination of Endogenous Expression of the Target Gene

In order to determine whether the target protein is produced in the selected cells, the cells were seeded at a cell density of 0.01 to $2 \times 10^6$ cells/ml preferably 0.5 to $1 \times 10^6$ cells/ml culture medium for 24 hours. The cell culture supernatant was removed later, cells were discarded, and the content of cell protein in the cell culture supernatant was determined by known methods, e.g., by a specific immunoassay for the respective protein.

In the case of EPO the content was determined by means of an ELISA. For this, streptavidin-coated microtitre plates were coated with biotinylated anti-EPO antibodies and incubated with a solution containing protein (1% w/v) to block unspecific binding. Then, 0.1 ml samples of culture supernatant was added and incubated overnight. After washing, peroxidase-conjugated monoclonal anti-EPO antibodies were added for 2 hours. The peroxidase reaction was carried out in a Perkin Elmer photometer at 405 nm using ABTS as a substrate.

The detection limit for EPO in this test was 10 pg EPO/ml. Cells which produced less than 10 pg EPO/ml when seeded at $10^6$ cells/ml were assessed as non producers and as suitable (+).

1.5 Determination of the Number of Copies of the Target Gene

In order to examine the number of copies of the target gene in the cell line, human genomic DNA was isolated from ca. $10^8$ cells and quantified following Sambrook et al., Molecular Cloning, A Laboratory Manual (1989), Cold Spring Harbor Laboratory Press. After cleaving the DNA with restriction enzymes, e.g., AgeI and AscI or BamHI, HindIII and SalI the DNA fragments were separated according to size by agarose gel electrophoresis and finally transferred onto a nylon membrane and immobilized.

The immobilized DNA was hybridized with a digoxigenin-labelled DNA probe which was specific for the locus of the target gene or for the chromosome on which the target gene was located and washed under stringent conditions. The specific hybridization signals were detected with the aid of standard chemiluminescence methodologies using radiation-sensitive films.

1.6 Determination of the Nucleic Acid Sequence of the Target Gene

The genomic DNA was isolated from ca. $10^7$ cells using a commercially available DNA isolation kit.

A pair of PCR primers was used to amplify the target gene. The sequences of these primers were complementary to sequences which flank the coding region of the target gene. This enabled the amplification of the entire coding region of the target gene.

The PCR product was either directly subjected to sequence analysis or cloned into a vector and subsequently sequenced. Sequencing primers which are complementary to sequences from the intron regions of the target gene were used, so that the sequences of the exon regions of the target gene could be obtained completely. The sequencing was carried out on an automated sequencer using commercially available materials and instructions.

1.7 Determination of the Glycosylation Pattern

In order to determine the glycosylation pattern of EPO, the cell lines to be tested were transfected with the plasmid pEPO 227 which contains a 4 kb HindIII/EcoRI fragment of the human EPO gene sequence under the control of the SV40 promoter (Jacobs et al. *Nature* 313 (1985), 806; Lee-Huang et al. *Gene* 128 (1993), 272). The cells were transfected in the presence of lipofectamine using a commercially available reagent kit according to the manufacturer's instructions. The EPO content was determined by ELISA in the cell supernatant isolated 2 to 5 days later.

The cell supernatant was concentrated and compared to known EPO products by isoelectric focusing (Righetti P. G., in: Work T. S., Burdon R. H. (ed.), Isoelectric focusing: Theory, methodology and applications, Elsevier Biomedical Press, Amsterdam (1983)). Human cells which yielded a comparable glycosylation pattern to known EPO products, e.g., urinary EPO were assessed as suitable (+).

1.8 Determination of Viral Contamination 1.8.1. Analyses by Means of Cell Culture In order to determine viral contamination of human cell lines tested lysates of the cells were incubated with a detector cell line in order to detect cytopathic effects. Hemadsorption analyses were also carried out.

In order to produce the lysate, a suspension of $10^6$ cells was lysed in 1 ml buffer by a rapid freeze-thaw process. The cellular residue was separated by centrifugation and the supernatant was added to the detector cell lines. HepG2 (ATCC HB-8065; *Nature* 282 (1979), 615–616), MRC-5 (ATCC-1587) and Vero (ATCC CCL-171; Jacobs, *Nature* 227 (1970), 168–170) cells were used as detector cell lines. Polio, SV, and influenza type viruses were used as a positive control. Detector cell lines that had been cultured without lysate were used as negative control. In order to determine cytopathic effects the detector cell lines were regularly examined over a period of at least 14 days.

For hemadsorption analysis, Vero cells which had been incubated with the cell lysates or is with the controls were admixed, after 7 days, with erythrocytes from chickens, pigs or humans. An attachment of the erythrocytes to the monolayer of cultured cells indicates viral contamination of the cultures.

1.8.2. In vivo Analysis

Lysates of the cell lines to be examined were prepared as stated in 1.8.1 and injected intraperitoneally or intracerebrally into newborn mice (0.1 ml per injection). The mice were observed with regard to morbidity and mortality over a period of 14 days.

1.8.3 Specific Detection of Viral Proteins

The presence of specific viral proteins, e.g., Epstein-Barr virus proteins (nuclear protein or capsid antigen) was tested by adding human serum of EBV-positive bands to immobilized cells of the cell line to be tested. The virus antigens were then detected by adding complement and the corresponding anti-human complement C3 fluorescein conjugate (to detect the nuclear antigen) or via anti-human globulin fluorescein (to detect the capsid antigen).

The human cell lines HepG2, HT 1080, Namalwa, HeLa, and HeLaS3 were tested as described. The results are set forth at Table 1.

It can be seen from table 1 that cell lines HT1080, Namalwa and HeLa S3 satisfied the required and preferred criteria with Namalwa and HeLa S3 being particularly preferred.

EXAMPLE 2

Cloning of EPO Homology Regions

Homology regions of the EPO gene were amplified by PCR using human placenta genomic DNA. For this, two PCR products were prepared from a 6.3 kB long homology region from the region of the 5'-untranslated sequences of the EPO gene, exon 1 and intron 1 (cf FIG. 1). The primers used to prepare the PCR product 1 had the following sequences: 5'-CGCGGCGGAT CCCAGGGAGC TGGGT-TGACC GG-3' (SEQ ID NO: 1) and 5'-GGCCGCGAAT TCTCCGCGCC TGGCCGGGGT CCCTCAGC-3' (SEQ ID NO: 2). The primers used to prepare the PCR product 2 had the following sequences: 5'-CGCGGCGGAT CCTCTC-CTCC CTCCCAAGCT GCAATC-3' (SEQ ID NO: 3) and 5'-GGCCGCGAAT TCTAGAACAG ATAGCCAGGC TGAGAG-3' (SEQ ID NO: 4).

Figure 2:
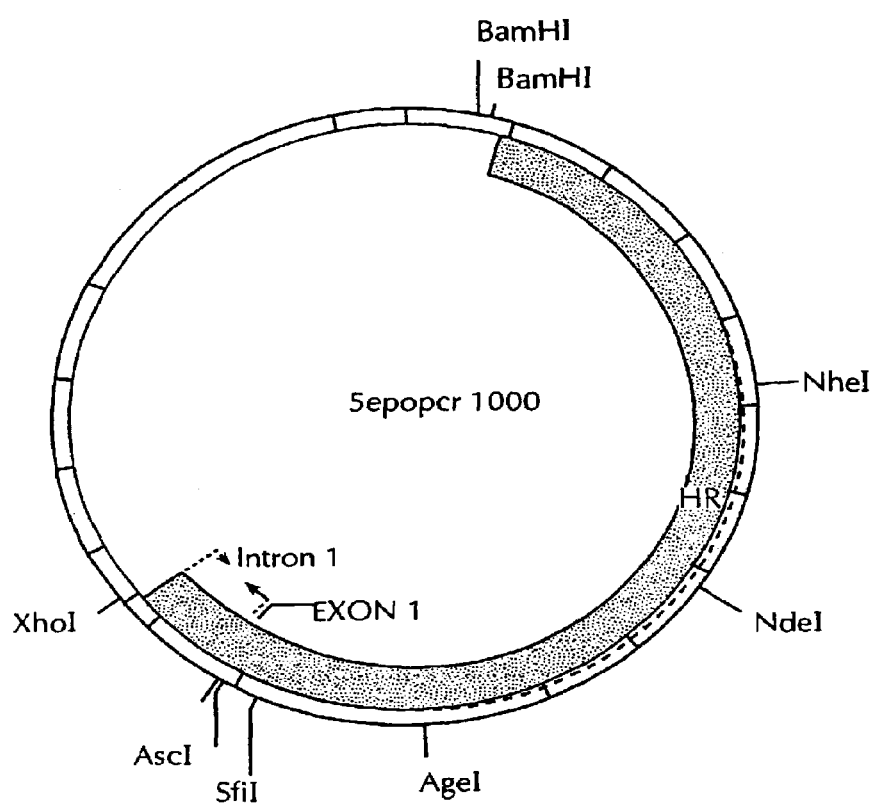
FIG. 2 shows a schematic representation of a plasmid which contains EPO homology regions from the region of the 5' untranslated sequences, exon 1 and intron 1.

The desired segments were cut out of the PCR products 1 and 2 by restriction cleavage (PCR product 1: HindIII, PCR product 2: HindIII and EcoRV) and cloned into the vector pCRII which had been cleaved with HindIII ,and EcoRV. The recombinant vector obtained in this manner was named 5epopcr1000 (cf. FIG. 2).

EXAMPLE 3

Figure 3:
FIG. 3 shows a schematic representation of a gene activation sequence which contains the Rous-sarcoma virus promoter (RSV), the neomycin phosphotransferase gene (NEO), the early polyadenylation region of SV40 (SVI pA), the early SV40 promoter (SVI), the dihydrofolate reductase gene (DHFR), an additional early SV40 polyadenylation region and the cytomegalovirus immediate-early promoter and enhancer (MCMV)
Figure 4A:
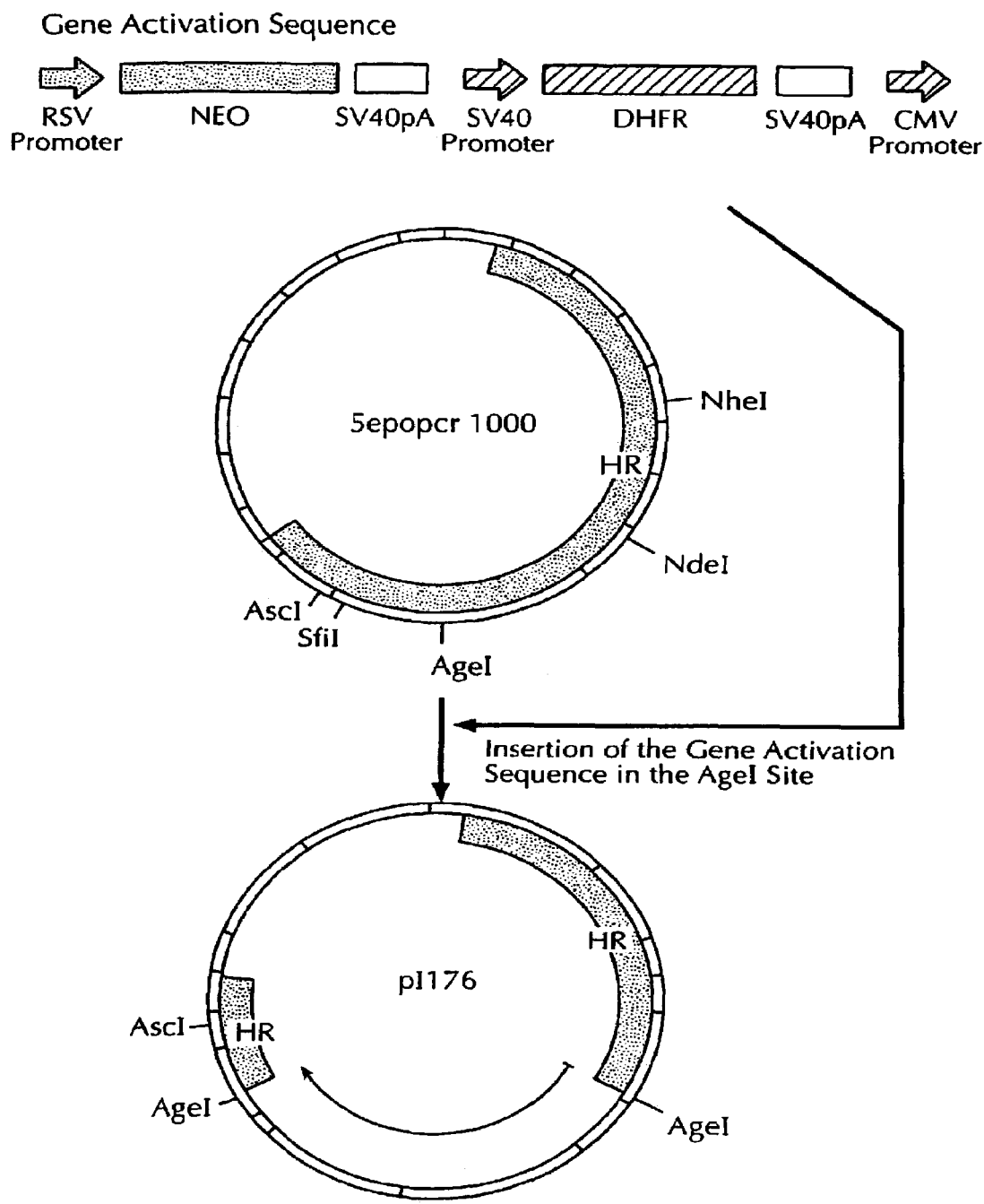
FIG. 4a shows the construction of the EPO gene targeting vector p176.
Figure 4B:
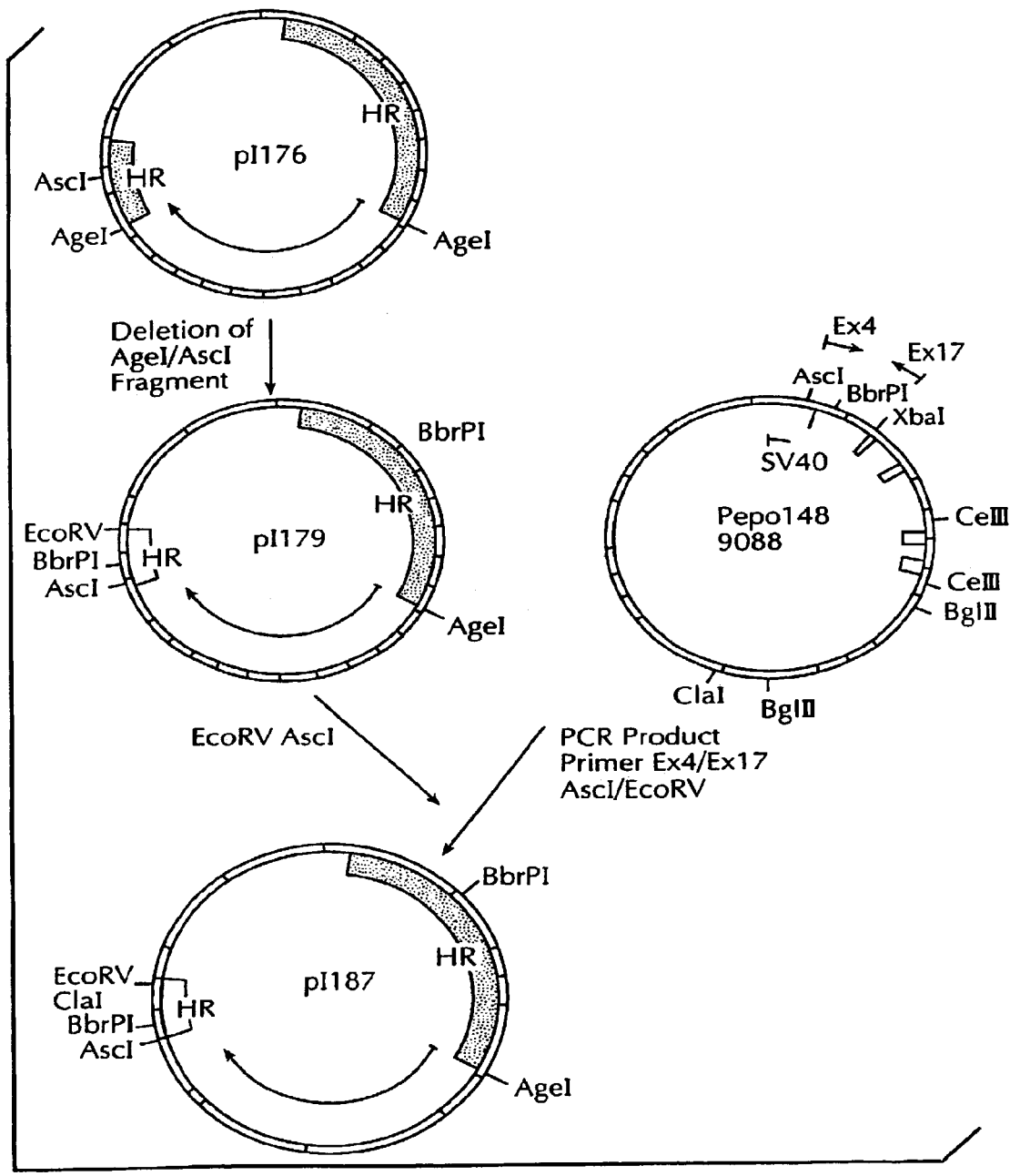
FIG. 4b shows the construction of the EPO gene targeting vectors p179 and p187.

Construction of EPO Gene Targeting Vectors 3.1 A gene activation sequence which contains the NEO gene, the DHFR gene and a CMV promoter/enhancer (cf. FIG. 3) was inserted into the AgeI site of the plasmid 5epocr1000 containing the EPO homology region to obtain the plasmid p176(cf. FIG. 4a). In order to bring the CMV promoter as close as possible to the translation start site of the EPO gene, a 963 bp long segment was deleted between the restriction sites AscI and AgeI (partial cleavage) to obtain the plasmid p179 (FIG. 4b).

3.2 In order to optimize expression, nucleotides in exon 1 which code for the beginning of the EPO leader sequence Met-Gly-Val-His were replaced by the synthetic sequence Met-Ser-Ala-His. This sequence was obtained as a template using appropriate primers by amplifying a genomic EPO DNA sequence, e.g., of the plasmid pEPO148 which contains a 3.5 kB BstEII/EcoRI fragment (including exons 1–5) of the human EPO gene sequence under the control of the SV40 promoter (Jacobs et al., *Nature* 313 (1985), 806 and Lee-Huang et al., Gene 128 (1993), 227). The plasmid p187 was obtained in this process (FIG. 4b).

Figure 4C:
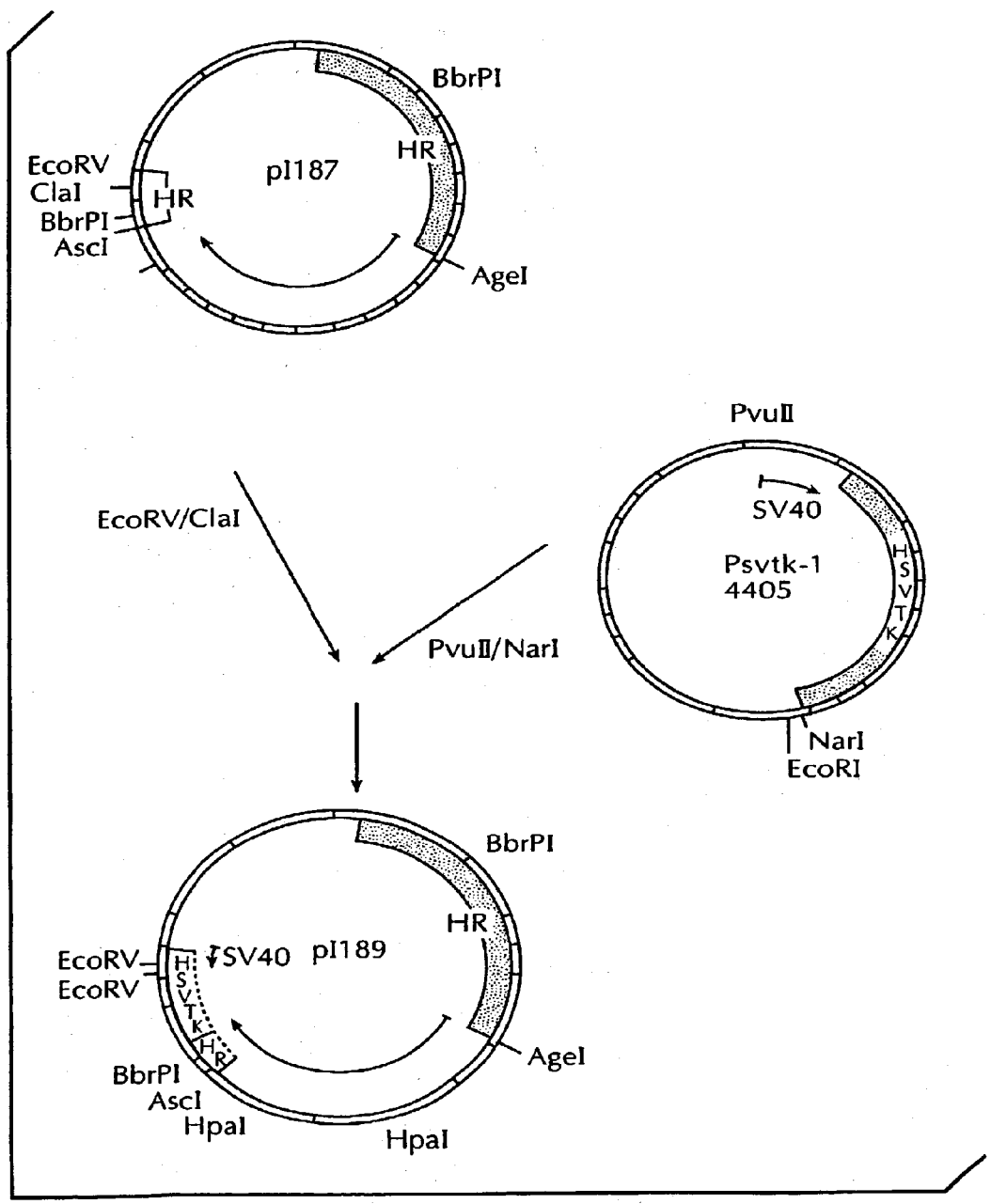
FIG. 4c shows the construction of the EPO gene targeting vector p189 (DSM 11661)

3.3 The plasmid p189 was prepared from the plasmid p187 by insertion of the Herpes Simplex virus thymidine kinase gene (HSV-TK) which was derived from Psvtk-1 (PvuII/NarI fragment) (FIG. 4c). The HSV-TK gene is under the control of the SV40 promoter and the 3' end of intron 1 (EcoRV/ClaI) in the opposite orientation relative to the CMV promoter and should serve to negatively select for homologous recombination.

Figure 4D:
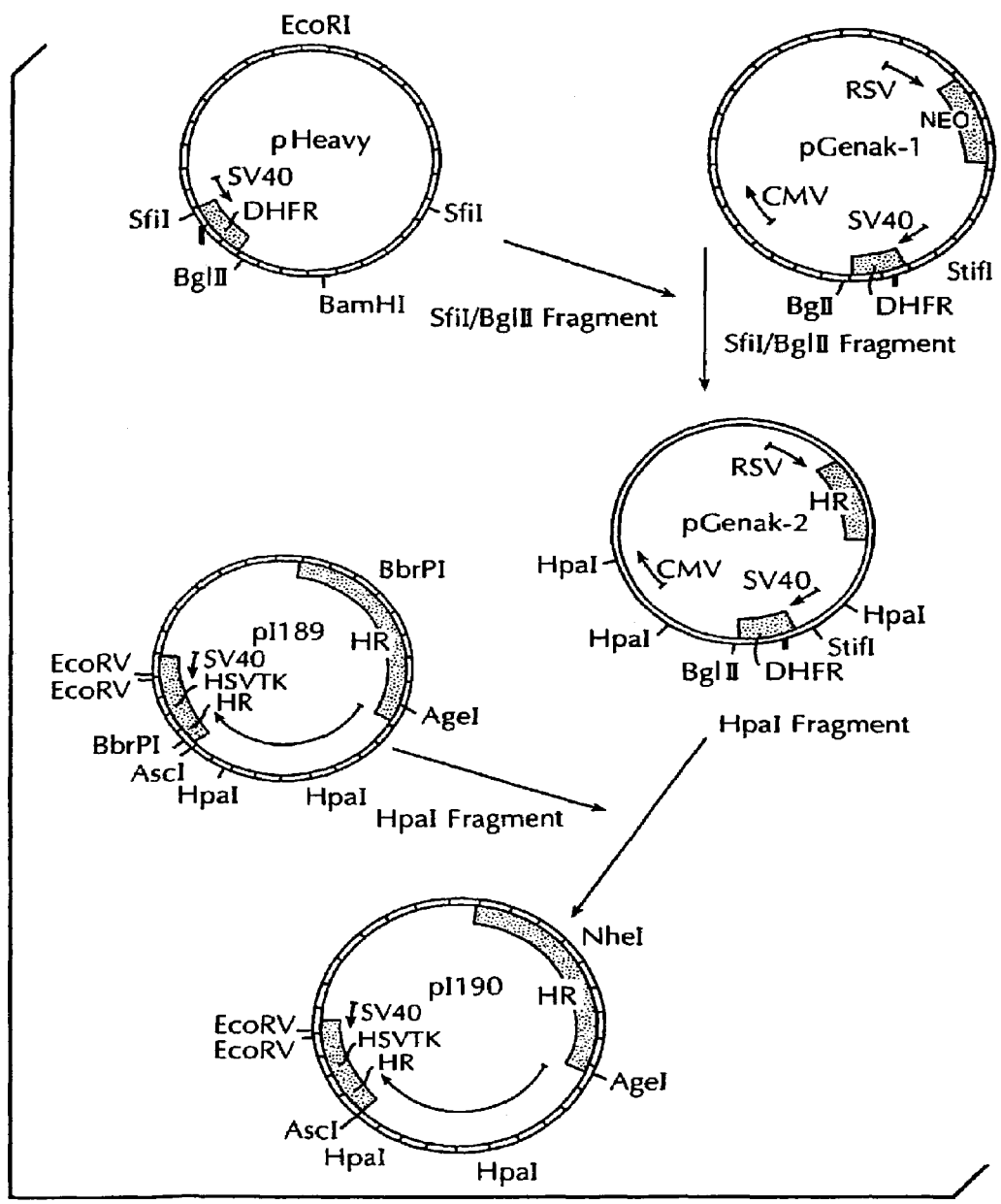
FIG. 4d shows the construction of the EPO gene targeting vector p190.

3.4 For the construction of plasmid p190, a SfiI/BglII fragment of pHEAVY, a plasmid which contains the cDNA of an arginine mutant of DHFR described by Simonsen et al. (*Proc. Natl. Acad. Sci. USA* 80 (1983), 2495) was subcloned into the plasmid pGenak-1 cleaved with SfiI and BglII. This plasmid contains the NEO gene under the control of the RSV promoter and the late SV40 polyadenylation site as a terminator, the murine DHFR gene under the control of the early SV40 promoter and the early SV40 polyadenylation site as a terminator (Kaufmann et al., *Mol. Cell. Biol.* 2 (1982), 1304; Okayama et al., *Mol. Cell. Biol.* 3 (1983), 280 and Schimke, *J. Biol. Chem.* 263 (1988), 5989) and the CMV promoter (Boshart et al., *Cell* 41 (1995), 521). Afterwards an HpaI fragment which contained the CDNA coding for the DHFR arginine mutant was ligated into the plasmid p189 cleaved with HpaI to obtain the plasmid p190 (FIG. 4d).

Figure 4E:
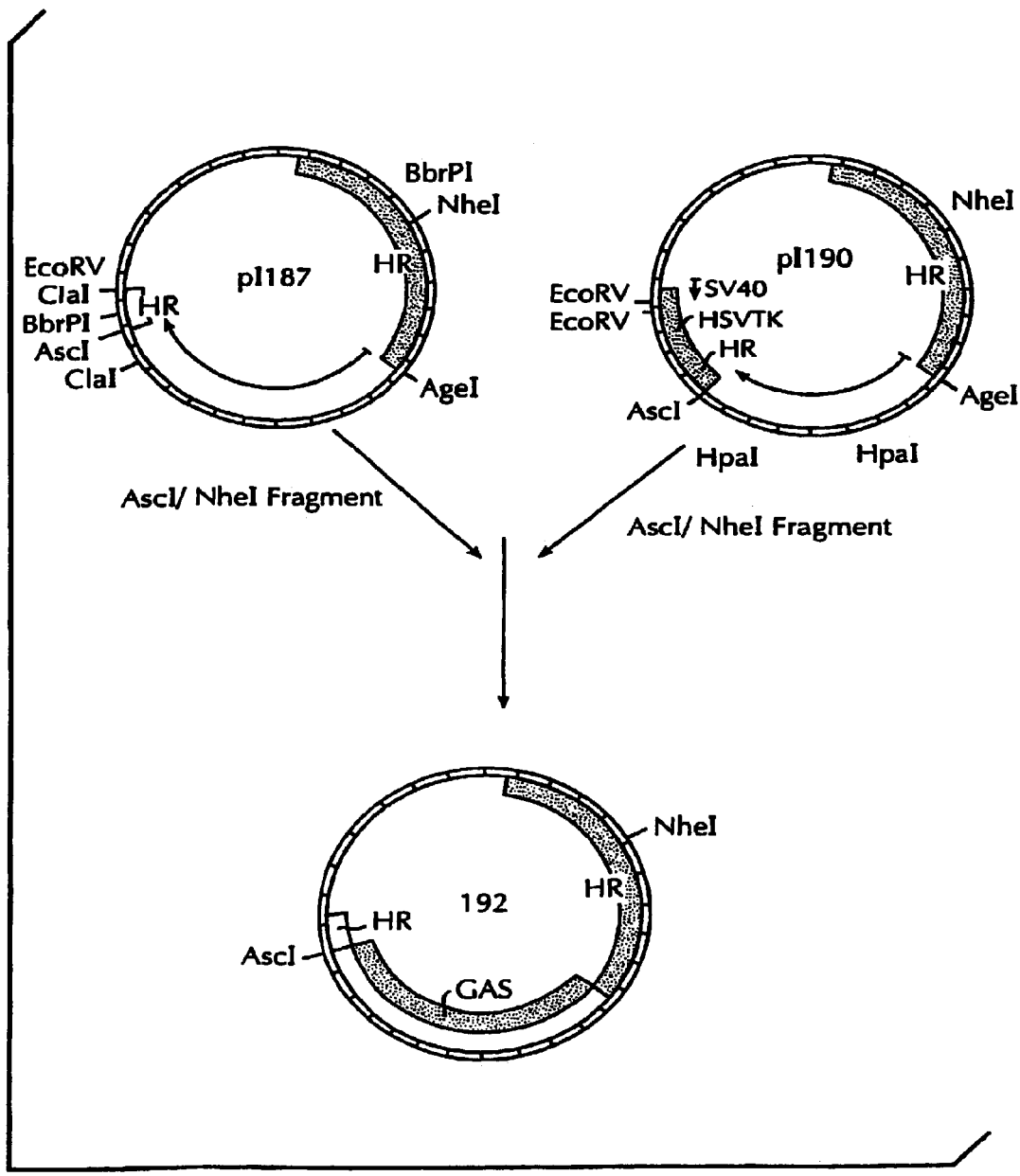
FIG. 4e shows the construction of the EPO gene targeting vector p192.

3.5 In order to obtain a trans fection vector without the HSV-TK gene, an AscI/NheI fragment of the plasmid p190 which contained the gene activation sequence was ligated into the AscI/NheI fragment of the plasmid p187 containing the exon 1. The resulting plasmid was named p192 (FIG. 4e).

EXAMPLE 4

Transfection of Cells

Various cell lines were selected for the production of EPO and transfected with targeting vectors.

4.1 Namalwa Cells

Namaiwa cells were cultured in T150 tissue culture flasks and transfected by electroporation ($1\times10^7$ cells/800 µl electroporation buffer 20 mM Hepes, 138 mM NaCl, 5 mM KCl, 0.7 mM $Na_2HPO_4$, 6 mM D-glucose monohydrate pH 7.0, 10 µg linearized DNA, 960 µF, 260 V BioRad gene pulser). After the electroporation the cells were cultured in RPMI 1640, 10% (v/v) fetal calf serum (FCS), 2 mM L-glutamine, 1 mM sodium pyruvate in forty 96-well plates. After two days the cells were cultured for 10 to 20 days in medium containing 1 mg/ml G-418. The supernatant was tested in a solid phase ELISA for the production of EPO as described sura. The EPO producing clones were expanded in 24-well plates and T-25 tissue culture flasks. Aliquots were frozen and the cells were subeloned by FACS (Ventage, Becton Dickinson). The subdlones were repeatedly tested for EPO production.

4.2 HT 1080 Cells

The conditions were as described for the Namalwa cells except that the HT1080 cells were cultured in DMEM, 10% (v/v) FCS, 2 mM L-glutamine, 1 mM sodium pyruvate. For transfection by electroporation, cells were detached from the walls of the culture vessels by trypsinization. After electroporation $1\times10^7$ cells were cultured in DMEM, 10% (v/v) FCS, 2 mM L-glutamine, 1 mM sodium pyruvate in 5 96-well plates.

4.3 HeLa S3 Cells

Conditions were as described for the Namalwa cells except that the HeLa S3 cells were cultured in RPMI 1640, 10% (v/v) FCS, 2 mM L-glutamine, 1% (v/v) NEM nonessential amino acids, 1 mM sodium pyruvate. For the transfection by electroporation the cells were detached from the walls of the culture vessels by trypsinization. The conditions for the electroporation were 960 µF/250 V. After the electroporation the cells were cultured in RPMI 1640, 10% (v/v) FCS, 2 mM L-glutamine, 1% (v/v) NEM, 1 mM sodium pyruvate in T75 tissue culture flasks. 24 hours after electroporation the cells were trypsinized and cultured for 10 to 15 days in a medium containing 600 µg/ml G-418 in 10 96-well plates.

EXAMPLE 5

Selection of EPO Producing Clones

The culture supernatant of transfected cells was tested in an EPO ELISA, as described supra. All steps were carried out at room temperature. 96-well plates pre-coated with streptavidin were coated with biotinylated anti-EPO antibodies. For coating, the plates were first washed with 50 mM sodium phosphate pH 7.2, 0.05% (v/v) Tween 20. Then 0.01 ml coating buffer (4 µg/ml biotinylated antibody, 10 mM sodium phosphate pH 7.2, 3 g/l bovine serum albumin, 20 g/l sucrose, 9 g/l NaCl) was added to each well and incubated for 3 hours at room temperature. Then the plates were washed with 50 mM sodium phosphate pH 7.2, dried and sealed.

Before the test and after washing three times with 0.3 ml phosphate-buffered saline (PBS), 0.05% Tween 20 (Sigma), the plates were incubated overnight with 0.2 ml PBS, 1% (w/v) protein per well in order to block unspecific binding.

After removing the blocking solution 0.1 ml culture supernatant was added and the plates were incubated overnight. The individual wells were each washed three times, with 0.3 ml PBS, 0.05% Tween 20. Then 100 µl peroxidase (POD) conjugated monoclonal anti-EPO antibody was added for 2 hours. The wells were each subsequently washed, three times, with 0.3 ml PBS, 0.05% Tween 20. Then the peroxidase reaction was carried out using ABTS as the substrate in a Perkin Elmer photometer at 405 nm. A standard calibration curve using recombinant EPO from CHO cells was used to calculate the EPO concentrations.

EXAMPLE 6

EPO Gene Amplification

In order to increase the EPO expression, the EPO producing clones were cultured in the presence of increasing concentrations (100 pM–1000 nM) of methotrexate (MTX). At each MTX concentration the clones were tested by an ELISA (see example 1.4) for the production of EPO. Strong producers were subcloned by limiting dilution.

EXAMPLE 7

Signal Sequence Mutations

Figure 5:
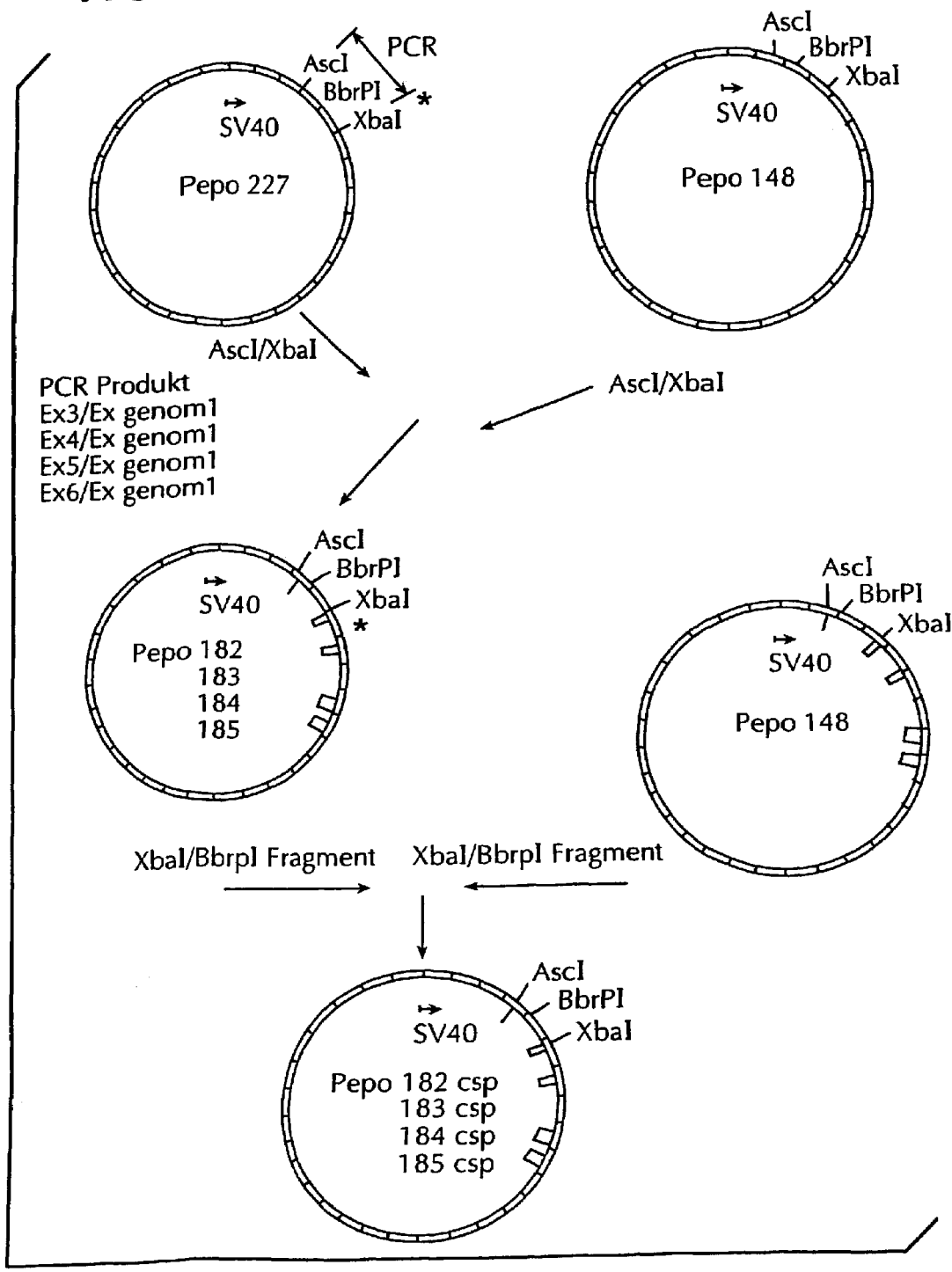
FIG. 5 shows a schematic representation of the construction of EPO cDNA with signal sequence mutations.

In order to optimize the leader sequence of the EPO molecule, the first four amino acids coded by exon 1 were substituted. Primers with various sequences (SEQ ID NOS: 4–17; the 3' primer contained a CelII site to select modified sequences) were used to obtain an AscI/XbaI fragment as a template by PCR using the plasmid pEPO227 which contains a 4 kB HindIII/EcoRI fragment (including exons 1–5) of the human EPO gene sequence under the control of the SV40 promoter (Jacobs et al., *Nature* 313 (1985), 806; Lee-Huang et al., Gene 128 (1993), 227). The resulting fragments were subsequently cloned into the plasmid pEPO 148 (example 3.2) to obtain the plasmids pEPO 182, 183, 184 and 185 (FIG. 5). The EPO gene expression was driven by an SV40 promoter. COS-7 cells were transiently transfected with the constructs (DEAE-dextan method) and the cells were tested for EPO production 48 hours after the transfection.

The mutated leader sequence Met-Ser-Ala-His obtained in this manner with the best EPO expression was used to construct gene targeting vectors (cf. example 3.2).

EXAMPLE 8

Characterization of Cell Lines Producing EPO

Three different cell lines (Namalwa, HeLa S3 and HT 1080) were selected for EPO gene activation. EPO producing clones were obtained by transfection with the plasmids p179, p187, p189, p190 or p192, described supra.

About 160,000 NEO resistant clones were tested for EPO production, of which 12–15 secreted EPO reproducibly into the cell supernatant in significant yield.

Of these clones it was surprisingly possible to identify a total of 7 EPO clones which produced EPO in adequate amounts for a large-scale production without gene amplification by MTX. This is a surprisingly high yield. The EPO production of these clones was in the range of from more than about 200 ng/ml up to more than about 1000 ng/ml/$10^6$ cells/24 hours.

After gene amplification with 500 nM MTX it was possible to increase the EPO production of the identified EPO clones to more than about 3000 ng/ml/$10^6$ cells/24 hours. Further increase of the MTX concentration to 1000 nM led to production of more than about 7000 ng/ml/$10^6$ cells/24 hours.

The clones obtained produced EPO even under serum-free culture conditions.

EXAMPLE 9

Characterization of the Genome of the EPO Producing Clones 9.1 Methods

Human genomic DNA was isolated from ca. $10^8$ cells and quantified, following Sambrook et al., supra. After cleavage of the genomic DNA with restriction enzymes; e.g., AgeI and AscI or BamHI, HindIII and SalI, the DNA fragments were separated according to their size by agarose gel electrophoresis and subsequently transferred and immobilized on a nylon membrane.

The immobilized DNA was hybridized with digoxigenin-labelled EPO-specific or gene activation sequence-specific DNA probes and washed under stringent conditions. The specific hybridization signals were detected with the aid of a chemiluminescent method using radiation sensitive films.

9.2 Results

Figure 6A:
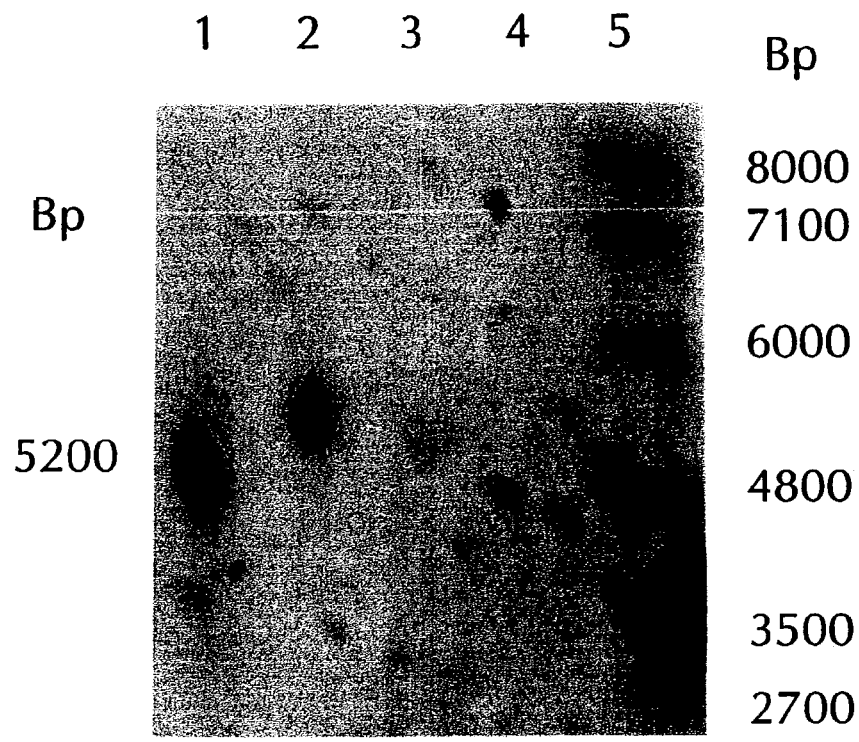
FIG. 6a shows the hybridization of cellular DNA with a probe from the CMV region of the gene cassette shown in FIG. 3; lanes 1 to 4 each show DNA from human cells, cleaved with the restriction enzymes AgeI and AscI; lane 1: EPO-producing HeLa S3 cell amplified with 1,000 nM methotrexate (MTX); lane 2: EPO-producing HeLa S3 cell amplified with 500 nM MTX; lane 3: EPO-producing HeLa S3 cell without amplification; lane 4: HeLa S3 cell without activated EPO gene; lane 5: digoxigenin-labelled length marker. The size of the hybridizing fragment in lanes 1 to 3 is ca. 5,200 bp.

The treatment of cells with 500 nM MTX led to an amplification of the hybridization signal in the EPO locus by a factor of 5 to 10. When it was increased further to 1000 nM MTX, amplification of >10 was obtained (FIG. 6a).

Figure 6B:
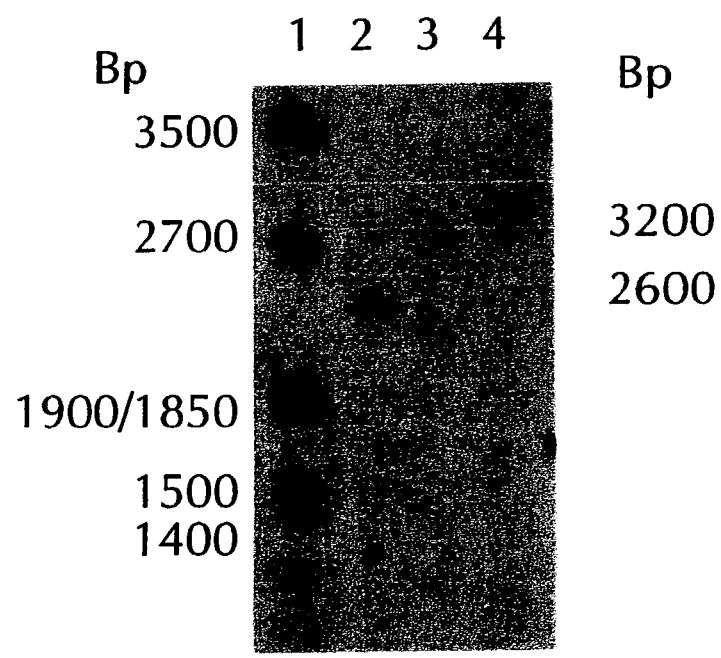
FIG. 6b shows the hybridization of a probe from the coding region of EPO with DNA of human cells. Lane 1 shows digoxigenin-labelled length markers; lanes 2 to 4 show DNA from human cells, cleaved with the restriction enzymes BamHI, HindIII and SalI; lane 2: EPO producing HeLa S3 cell amplified with 500 nM MTX (length of the band produced by the non-activated endogenous gene: 3,200 bp; length of the copy of the EPO gene activated by gene targeting: 2,600 bp); lane 3: DNA from a non-amplified EPO-producing HeLa S3 cell; lane 4: DNA from a HeLa S3 control cell.

In the case of hybridization with an EPO-specific probe, the copies of the chromosome 7 which were not affected by homologous recombination were also detected. As can be seen in FIG. 6b, these DNA fragments which also hybridize have a different size that is clearly distinguishable and their signal strength was not changed by the use of MTX.

EXAMPLE 10

Purification of EPO from Culture Supernatants of Human Cell Lines (HeLa S3; Namalwa and HT1080)

Two methods were used to purify EPO from cell culture supernatants of human cell lines. These differed in the number and principle of the chromatography steps and were used depending on the composition of the medium and the EPO concentrations. In these experiments, EPO was purified from cell free supernatant of cultured HeLaS3 cells, where the cell culture medium included 2% (v/v) fetal calf serum.
Method 1: 1st step: blue Sepharose column
2nd step: butyl Sepharose column
3rd step: hydroxyapatite column
4th step: concentration
Method 2: 1st step: blue Sepharose column
2nd step: hydroxyapatite column
3rd step: concentration
(alternative 3rd step: RP-HPLC)

1. Blue Sepharose Column

A 5 ml blue Sepharose containing column was equilibrated with at least 5 column volumes (CV) buffer A (20 mM Tris-HCl, pH 7.0; 5 mM $CaCl_2$; 100 mM NaCl). Subsequently, 70 ml HeLa S3 cell supernatant (containing ca. 245 µg EPO and 70–100 mg total protein) was absorbed overnight at a flow rate of 0.5 ml/min in a circulation process.

The column was washed With at least 5 CVs buffer B (20 mM Tris-HCl, pH 7.0; 5 mM $CaCl_2$; 250 mM NaCl) and at least 5 CVs buffer C (20 mM Tris-HCl, pH 7.0; 0.2 mM $CaCl_2$, 250 mM NaCl) at 0.5 ml/min. The success of the washing was monitored by measuring the protein content at OD280.

EPO was eluted with buffer D (100 mM Tris-HCl, pH 7.0; 0.2 mM CaCl$_2$; 2 M NaCl) at a flow rate of 0.5 ml/min. The elution solution was collected in 1–2 ml fractions.

The EPO content of the fractions, the wash solutions and the flow through were determined by reverse phase (RP)-HPLC by applying an aliquot to a column. Alternatively an immunological dot-blot was carried out for the qualitative identification of fractions containing EPO.

Fractions containing EPO (8–12 ml) were pooled and applied to a butyl-Sepharose column.

The yield after the blue Sepharose column was ca. 175 µg EPO (corresponds to ca. 70%). In general the yield after blue Sepharose was between 50–75%.

2. Butyl Sepharose Column (Hydrophobic Interaction Chromatography)

A 2–3 ml butyl Sepharose column was prepared, equilibrated with at least 5 CV buffer D (100 mM Tris-HCl, pH 7.0; 0.2 mM CaCl$_2$; 2 M NaCl), and subsequently the blue Sepharose pool containing EPO from 1, supra (ca. 150 µg EPO) was absorbed at a flow rate of 0.5 ml/min.

The column was washed with at least 5 CV buffer E (20 mM Tris-HCl, pH 7.0; 2 M NaCl and 10% isopropanol) at 0.5 ml/min. The success of the washing was monitored by measuring the protein content at OD280.

EPO was eluted with buffer F (20 mM Tris-HCl, pH 7.0; 2 M NaCl and 20% isopropanol) at a flow rate of 0.5 ml/min. The elution solution was collected in 1–2 ml fractions.

The EPO content of the fractions, the wash solutions and the flow through were determined by RP-HPLC by applying an aliquot to a POROS R2/H column. Alternatively, an immunological dot-blot was carried out for the qualitative identification of fractions containing EPO.

Fractions containing EPO (10–15 ml) were pooled and applied to a hydroxyapatite column.

The yield after the butyl Sepharose column was ca. 130 µg EPO (corresponds to ca. 85%). In general the yield of the butyl Sepharose was between 60–85% of the applied blue Sepharose pool.

3. Hydroxyapatite Column

A 5 ml hydroxyapatite column was equilibrated with at least 5 CV buffer F (20 mM Tris-HCl, pH 7.0; 2 M NaCl; 20% isopropanol) and subsequently the butyl Sepharose pool containing EPO from 2, supra (ca. 125 µg EPO) was absorbed at a flow rate of 0.5 ml/min.

The column was washed with at least 5 CV buffer G (20 mM Tris-HCl, pH 7.0; 2 M NaCl) at 0.5 ml/min. The success of the washing was monitored by measuring the protein content at OD280.

EPO was eluted with buffer H (10 mM Na-phosphate, pH 7.0; 80 mM NaCl) at a flow rate of 0.5 ml/min. The elution solution was collected in 1–2 ml fractions.

The EPO content of the fractions, the wash solutions and the eluant were determined by RP-HPLC by applying an aliquot to a POROS R2/H column.

Fractions containing EPO (3–6 ml) were pooled. The yield of the hydroxyapatite column was ca. 80 µg EPO (corresponds to ca. 60%). In general the yield of the hydroxyapatite column was between 50–65% of the applied butyl Sepharose pool.

4. Concentration

The pooled EPO fractions from the hydroxyapatite step were concentrated in centrifugation units with an exclusion size of 10 kD to a concentration of 0.1–0.5 mg/ml, admixed with 0.01% Tween 20 and stored in aliquots at −20° C.

Yield Table:

|  | EPO (µg) | Yield (%) |
|---|---|---|
| Initial | 245 | 100 |
| blue Sepharose | 175 | 70 |
| butyl Sepharose column | 130 | 53 |
| hydroxyapatite column | 80 | 33 |
| concentration | 60 | 25 |

The purity of the isolated EPO was about >90%, usually even >95%.

Method 2 was also used to increase the EPO yield in which the butyl Sepharose step was omitted. This method can be applied above all to cell culture supernatants without or with the addition of 1% (v/v) FCS and yields isolated EPO of approximately the same purity (90–95%).

The presence of 5 mM CaCl$_2$ in the equilibration buffer (buffer F) for the hydroxyapatite column led to improved binding in this method and thus also to reproducible elution behavior of EPO in the hydroxyapatite step. Hence, method 2 was carried out with the following buffers using basically the same process as method 1:

1. Blue Sepharose Column

| | |
|---|---|
| equilibration buffer (buffer A): | 20 mM Tris-HCl, pH 7.0; 5 mM CaCl$_2$; 100 mM NaCl |
| wash buffer 1 (buffer B): | 20 mM Tris-HCl, pH 7.0; 5 mM CaCl$_2$; 250 mM NaCl |
| wash buffer 2 (buffer C): | 20 mM Tris-HCl, pH 7.0; 5 mM CaCl$_2$, 250 mM NaCl |
| Elution buffer (buffer D): | 100 mM Tris-HCl, pH 7.0; 5 mM CaCl$_2$; 2 M NaCl |

2. Hydroxyapatite Column

| | |
|---|---|
| equilibration buffer (buffer F): | 50 mM Tris-HCl, pH 7.0; 5 mM CaCl$_2$; 1 M NaCl |
| wash buffer (buffer G): | 10 mM Tris-HCl, pH 7.0; 5 mM CaCl$_2$; 80 mM NaCl |
| elution buffer (buffer H): | 10 mM Na phosphate, pH 7.0; 0.5 mM CaCl$_2$; 80 mM NaCl |

Yield Scheme:

|  | EPO (µg) | Yield (%) |
|---|---|---|
| initial | 600 | 100 |
| blue Sepharose | 450 | 75 |
| hydroxyapatite column | 335 | 55 |
| concentration | 310 | 52 |

The addition of 5 mM CaCl$_2$ in buffers C, D, E, F, and G in method 1 also led to improved binding and more defined elution from the hydroxyapatite column.

EXAMPLE 11

Determination of the Specific Activity in Vivo of EPO from Human Cell Lines (Bioassay on the Normocytaemic Mouse)

The dose-dependent activity of EPO on the proliferation and differentiation of erythrocyte precursor cells was determined in vivo in mice via the increase of reticulocytes in the blood after administration of EPO.

For this, groups of eight mice received various doses of the EPO sample to be analyzed, and of an EPO standard (matched with the EPO WHO standard). The mice were subsequently kept under constant defined conditions. Four days after administration of EPO, blood was collected from the mice and the reticulocytes were stained with acridine orange. The reticulocyte number per 30,000 erythrocytes was determined by microfluorimetry in a flow cytometer by analyzing the red fluorescence histogram.

The biological activity of the cells was calculated from the values for the reticulocyte numbers of the sample and of the standard at the various doses according to the method described by Linder of paired quantity determination with parallel lines (A. Linder, "Planen und Auswerten von Versuchen," 3rd edition, 1969, Birkenhäuser Verlag Basel).

Result:

| EPO from the cell line | specific activity U/mg |
| --- | --- |
| HeLa S3 (sample 1) | 100,000 |
| HeLa S3 (sample 2) | 110,000 |

We claim:

1. A DNA construct useful in homologous recombination, comprising:

(i) a pair of flanking DNA sequences which are homologous to regions of the human gene which encodes erythropoietin, said regions being selected from the group consisting of 5'-untranslated sequences, a modified portion of exon 1, and intron 1, to permit homologous recombination, said modified portion of exon 1 corresponding to the first four codons of the signal sequence coding region, and coding for a sequence of four amino acids of formula Met Xaa Xaa Xaa (SEQ ID NO: 5)

wherein the first Xaa is Gly or Ser, the second Xaa is Ala, Val, Leu, Ile, Ser or Pro, and the third Xaa is Pro, Arg, Cys or His, with the proviso that said four amino acid sequence is not Met Gly Val His (SEQ ID NO: 6).

(ii) a gene which codes for a positive selection marker, and (iii) a heterologous expression control sequence which comprises a promoter.

2. The DNA construct of claim 1, wherein Met Xaa Xaa Xaa is (a)  Met-Gly-Ala-His    (SEQ ID NO:7)
(b)  Met-Ser-Ala-His    (SEQ ID NO:8)
(c)  Met-Gly-Val-Pro    (SEQ ID NO:9) or
(d)  Met-Ser-Val-His    (SEQ ID NO:10).

3. The DNA construct of claim 1, further comprising an amplifiable gene.

4. Plasmid p189 (DSM 11661).

5. The DNA construct of claim 1 comprising a translation start site, wherein the heterologous expression control sequence is positioned within 1100 nucleotides of the translation start site.

* * * * *